US012195769B2

(12) United States Patent
Putseys et al.

(10) Patent No.: US 12,195,769 B2
(45) Date of Patent: *Jan. 14, 2025

(54) LIPOLYTIC ENZYME VARIANTS

(71) Applicant: DSM IP ASSETS B.V., Heerlen (NL)

(72) Inventors: Joke Anneleen Putseys, Echt (NL); Neil Carr, Echt (NL); René Marcel De Jong, Echt (NL); Aloysius Wilhelmus Rudolphus Hubertus Teunissen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 922 days.

This patent is subject to a terminal disclaimer.

(21) Appl. No.: 17/253,266

(22) PCT Filed: Jun. 18, 2019

(86) PCT No.: PCT/EP2019/065992
§ 371 (c)(1),
(2) Date: Dec. 17, 2020

(87) PCT Pub. No.: WO2019/243312
PCT Pub. Date: Dec. 26, 2019

(65) Prior Publication Data
US 2021/0115418 A1    Apr. 22, 2021

(30) Foreign Application Priority Data

Jun. 19, 2018   (EP) ..................... 18178445

(51) Int. Cl.
| | | |
|---|---|---|
| C12N 15/00 | (2006.01) |
| A21D 6/00 | (2006.01) |
| A21D 8/04 | (2006.01) |
| C12N 9/16 | (2006.01) |
| C12N 9/18 | (2006.01) |
| C12N 9/20 | (2006.01) |

(52) U.S. Cl.
CPC ............. *C12N 9/20* (2013.01); *A21D 6/00* (2013.01); *A21D 8/042* (2013.01); *C12Y 301/01003* (2013.01)

(58) Field of Classification Search
None
See application file for complete search history.

(56) References Cited

U.S. PATENT DOCUMENTS

| | | | |
|---|---|---|---|
| 5,545,806 | A | 8/1996 | Lonberg et al. |
| 9,101,585 | B2 | 8/2015 | Fritsche et al. |
| 9,717,774 | B2 | 8/2017 | Fritsche et al. |
| 9,895,415 | B2 | 2/2018 | Fritsche et al. |
| 9,993,523 | B2 | 6/2018 | Fritsche et al. |
| 10,064,913 | B2 | 9/2018 | Weinschenk et al. |
| 10,357,540 | B2 | 7/2019 | Fritsche et al. |
| 10,420,816 | B1 | 9/2019 | Fritsche et al. |
| 2002/0197266 | A1 | 12/2002 | Debinski |
| 2003/0228446 | A1 | 12/2003 | Pearce |
| 2006/0228446 | A1 | 10/2006 | Borch et al. |
| 2011/0229504 | A1 | 9/2011 | Fritsche et al. |
| 2011/0262591 | A1 | 10/2011 | Van Der Laan et al. |
| 2012/0058222 | A1 | 3/2012 | Sorensen et al. |
| 2013/0045191 | A1 | 2/2013 | Weinschenk et al. |
| 2014/0147552 | A1 | 5/2014 | Van Der Laan et al. |
| 2015/0147347 | A1 | 5/2015 | Fritsche et al. |
| 2017/0204372 | A1 | 7/2017 | Mohler et al. |
| 2017/0304399 | A1 | 10/2017 | Fritsche et al. |
| 2017/0312336 | A1 | 11/2017 | Fritsche et al. |
| 2018/0000896 | A1 | 1/2018 | Fritsche et al. |
| 2018/0051080 | A1 | 2/2018 | Leonie et al. |
| 2018/0125929 | A1 | 5/2018 | Fritsche et al. |
| 2018/0319884 | A1 | 11/2018 | Leonie et al. |
| 2019/0290727 | A1 | 9/2019 | Fritsche et al. |

FOREIGN PATENT DOCUMENTS

| | | |
|---|---|---|
| DE | 102016115246 B3 | 12/2017 |
| WO | 1998026057 A1 | 6/1998 |
| WO | 2009106575 A1 | 9/2009 |
| WO | 2011113819 A2 | 9/2011 |
| WO | 2016011210 A2 | 1/2016 |
| WO | 2016156202 A1 | 10/2016 |
| WO | 2018033291 A1 | 2/2018 |
| WO | 2018114912 A1 | 6/2018 |

OTHER PUBLICATIONS

International Search Report issued in counterpart application No. PCT/EP2018/080176, mailed Jan. 17, 2019.
Hickman et al., "Antigen Selection for Enhanced Affinity T-Cell Receptor-Based Cancer Therapies" Journal of Biomolecular Screening. (2016) vol. 21(8) 769-785.
German Search Report of German Patent Application No. 102017125888.4 dated Oct. 12, 2018.
Smith, M. J. et al., "Analysis of differential gene expression in colorectal cancer and stroma using fluorescence-activated cell sorting purification," British Journal of Cancer BJC, vol. 100, pp. 1452-1464, 2009.
Tilman, Gaëlle et al., "Human periostin gene expression in normal tissues, tumors and melanoma: evidences for periostin production by both stromal and melanoma cells," Molecular Cancer, vol. 6, pp. 1-13, 2007.

(Continued)

*Primary Examiner* — Satyendra K Singh
(74) *Attorney, Agent, or Firm* — McBee Moore & Vanik IP, LLC

(57) ABSTRACT

The present invention relates to a variant polypeptide having a lipase activity, wherein the polypeptide may be a polypeptide that has an amino acid sequence which has at least 70% identity to a mature amino acid sequence of SEQ ID NO: 1 or SEQ ID NO: 6, wherein the polypeptide comprises an amino acid substitution at position 295 and at least one further amino acid substitution at position 113, 121, 179 and/or 284, wherein the positions are defined with reference to SEQ ID NO: 1 or SEQ ID NO: 6. The invention further relates to a process for preparing a dough wherein a polypeptide as disclosed herein is used and baked product prepared from the dough.

18 Claims, 2 Drawing Sheets

Specification includes a Sequence Listing.

(56) References Cited

OTHER PUBLICATIONS

Qiao, Jie, et al., "Stroma derived COL6A3 is a potential prognosis marker of colorectal carcinoma revealed by quantitative proteomics," OncoTarget, vol. 6, pp. 29929-29946, 2015.
Köhler, G., et al., "Derivation of specific antibody-producing tissue culture and tumor lines by cell fusion," European Journal of Immunology, vol. 7, pp. 511-519, 1976.
Haskard, D.O., et al., "The Production of Human Monoclonal Autoantibodies from Patients with Rheumatoid Arthritis by the EBV—Hybridoma Technique," Journal of Immunological Methods, vol. 74, pp. 361-367, 1984.
Huse, William D., et al., "Generation of a Large Combinatorial Library of the Immunoglobulin Repertoire in Phage Lambda," Science, vol. 246, pp. 1275-1281, 1989.
International Search Report for Application No. PCT/EP2019/065992 mailed Aug. 6, 2019.
S. P. C. Tait and T. Galliard, "Effect on baking quality of changes in lipid composition during wholemeal storage," Journal of Cereal Science, (1988), vol. 8, No. 2 : 125-137.
T. A. Clayton and W. R. Morrison, "Changes in Flour Lipids During the Storage of Wheat Flour," Journal of Science of Food & Agriculture, (1972), vol. 23, 721-735.

LIPOLYTIC ENZYME VARIANTS

CROSS-REFERENCE TO RELATED APPLICATIONS

This application is the National Stage entry of International Application No. PCT/EP2019/065992, filed 18 Jun. 2019, which claims priority to European Patent Application No. 18178445.5, filed 19 Jun. 2018.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03 (a)), a Sequence Listing in the form of an ASCII-compliant text file (entitled "Sequence_Listing_2919208-547000_ST25.txt" created on 17 Dec. 2020, and 14,575 bytes in size) is submitted concurrently with the instant application, and the entire contents of the Sequence Listing are incorporated herein by reference.

BACKGROUND

Field

The present invention relates to a variant polypeptide having lipolytic activity, a process for preparing a dough wherein the polypeptide is used, and a process for preparing a baked product.

Description of Related Art

In the baking industry, e.g. in the industrial dough and bread making, processing aids are commonly used to improve properties of a dough and or a baked product. Dough properties that may be improved comprise stability, gas retaining capability, elasticity, extensibility, moldability etcetera. Properties of the baked products that may be improved comprise loaf volume, crust crispiness, oven spring, crumb texture, crumb structure, crumb softness, flavour, relative staleness and shelf life.

It is known that dough made from wholemeal flour has a poorer stability than dough made from white flour Consequently, at the end of proof wholemeal dough loses more leavening gas and the volume of the baked product of the wholemeal dough is lower as compared to the volume of a baked product made from a white flour dough. In particular, during process handling when the dough is knocked or jarred, the dough volume is challenged and may be subject to partial collapse. Cereal flour contains a certain amount of lipids and free fatty acids, and during storage of flour the amount of free fatty acids in the flour usually increases, for instance due to lipolysis of endogenous lipids. This is mostly noted during storage of whole meal flour (see for instance Tait and Galliard, J Cereal Sci. 1988, 8:125-137 and Clayton and Morrison, Sci. Food Agric 1972, 23, 721-735) The amount of free fatty acids in flour influences dough properties such as dough stability, and properties of baked products made thereof.

Processing aids, such as chemical additives and enzymes are added to flour and/or dough to improve the properties of a dough or a baked product.

Chemical additives comprise emulsifiers, such as emulsifiers acting as dough conditioners such as diacetyl tartaric acid esters of mono/diglycerides (DATEM), sodium stearoyl lactylate (SSL) or calcium stearoyl lactylate (CSL). Emulsifiers such as DATEM may also be used to increase or control the volume of a baked product. There is a growing resistance of consumers to chemical emulsifiers and therefore there is a need for non-chemical alternatives.

Replacers of chemical emulsifiers are lipolytic enzymes that upon action on a substrate can generate emulsifying molecules in situ. For instance, lipases are used to fully or partly replace DATEM. WO1998026057 describes a phospholipase that can be used in a process for making bread. WO2009/106575 describes a lipolytic enzyme and its use in a process for making bread.

There is a need for improved lipolytic enzymes that can be used as processing aids in the preparation of baked product, for instance a wholemeal baked product.

SUMMARY

The present invention relates to a variant polypeptide having a lipase activity, wherein the polypeptide is selected from the group consisting of:
i. a polypeptide which comprises an amino acid sequence which has at least 70% identity to a mature amino acid sequence of SEQ ID NO: 1 or SEQ ID NO: 6, wherein the polypeptide comprises an amino acid substitution at position 295 and at least one further amino acid substitution at position 113, 121, 179 and/or 284, wherein the positions are defined with reference to SEQ ID NO: 1 or SEQ ID NO: 6;
ii. a polypeptide according to i), wherein the amino acid substitution at position 295 is D295G, D295N or D295S and the at least one further amino acid substitution at position 113 is I113H, I113N or I113T, at position 121 the amino acid substitution is N121D, at position 179 the amino acid substitution is V179M, and/or at position 284 the amino acid substitution is I284M or I284T;
iii. a polypeptide which has at least 70% identity to a mature amino acid sequence of SEQ ID NO: 1 or SEQ ID NO: 6, wherein the polypeptide comprises amino acid substitutions (D295S and V179M), (D295N and V179M), (D295S, I113H and V179M), (D295G and I113T), (D295N and I113N), (D295N, I113T, V179M, and N112D). (D295S, I113H, V179M, and I284M), (D295N and I113T), (D295S, I113T, V179M, and I284M), (D295S, I113T, V179M, N121D), (D295S, I113T and V179M), (D295S and I113N), or (D295N and I284T), wherein the substitutions are defined with reference to SEQ ID NO: 1 or SEQ ID NO: 6;
iv. a polypeptide according to i)-iii), wherein the amino acid sequence of SEQ ID NO: 1 or SEQ ID NO: 6 comprises an insertion of one or more amino acids after position 304
v. a polypeptide according to iv), a polypeptide according to iv), wherein the mature amino acid sequence of SEQ ID NO: 1 or SEQ ID NO: 6 comprises the insertion.

The invention also relates to a nucleic acid encoding a polypeptide having lipase activity as disclosed herein, wherein optionally the nucleic acid has at least 70% identity to SEQ ID NO: 2 or SEQ ID NO: 7, wherein the nucleic acid comprises a mutation encoding an amino acid substitution D295G, D295N or D295S and at least one further amino acid substitution I113H, I113N or I113T, and/or N121D, and/or V179M, and/or I284M or I284T, wherein the amino acid substitutions are defined with reference to SEQ ID NO:

1 or SEQ ID NO: 6, wherein the positions of the substitutions are defined with reference to SEQ ID NO:1 or SEQ ID NO: 6.

Also disclosed is an expression vector comprising a nucleic acid as disclosed herein operably linked to at least one control sequence that directs expression of the polypeptide in a host cell.

The invention further relates to a recombinant host cell comprising a nucleic acid as disclosed herein, or an expression vector as disclosed herein.

The invention further relates to a method for the preparation of a polypeptide as disclosed herein comprising cultivating a host cell in a suitable fermentation medium, under conditions that allow expression of the polypeptide, and optionally recovering the polypeptide.

The invention further relates to a process for preparing a dough comprising adding a polypeptide as disclosed herein or a composition comprising a polypeptide as disclosed herein to the dough and a dough comprising a variant polypeptide as disclosed herein.

The invention further relates to a process for preparing a baked product comprising baking a dough as disclosed herein.

Also disclosed is the use of a variant polypeptide as disclosed herein to increase the shock resistance of a dough or to increase the volume of a baked product.

SEQUENCE LISTING

Figure 1:
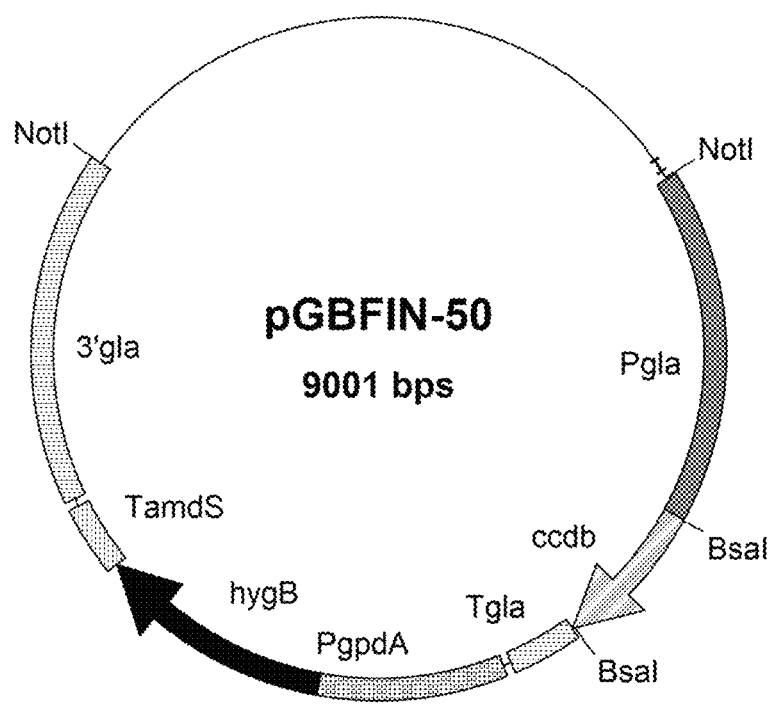
FIG. 1. Sets out the *Aspergillus* expression vector pGBFIN-50

SEQ ID NO: 1: Amino acid sequence of a polypeptide having lipase activity

SEQ ID NO: 2: Nucleotide sequence encoding a polypeptide having lipase activity according to SEQ ID NO: 1.

SEQ ID NO: 3: Amino acid sequence of a polypeptide having lipase activity according to SEQ ID NO: 1, having an insertion of two amino acids PP after position 304.

SEQ ID NO: 4: Nucleotide sequence encoding a polypeptide having lipase activity according to SEQ ID NO: 3

SEQ ID NO: 5: Modified translation initiation sequence of glucoamylase glaA promoter SEQ ID NO: 6: Amino acid sequence of *Fusarium oxysporum* lipase SEQ ID NO: 7: Nucleotide sequence encoding *Fusarium oxysporum* lipase that was codon-pair optimized for expression in *Aspergillus niger*

Definitions

The term 'baked product' refers to a baked food product prepared from a dough.

Examples of baked products, whether of a white, brown, or whole-grain such as whole-meal or whole-wheat type, include bread, typically in the form of loaves or rolls, French baguette-type bread, pastries, croissants, brioche, panettone, pasta, noodles (boiled or (stir-) fried), pita bread and other flat breads, tortillas, tacos, cakes, pancakes, cookies in particular biscuits, doughnuts, including yeasted doughnuts, bagels, pie crusts, steamed bread, crisp bread, brownies, sheet cakes, snack foods (e.g., pretzels, tortilla chips, fabricated snacks, fabricated potato crisps). Baked products are typically made by baking a dough at a suitable temperature for making the baked product such as a temperature between 100° C. and 300° C. A baked product as disclosed herein may be a whole-meal or a whole-wheat bread.

The term "dough" is defined herein as a mixture of flour and other ingredients. Usually, dough is firm enough to knead or roll. The dough may be fresh, frozen, prepared or parbaked.

Dough is usually made from basic dough ingredients including (cereal) flour, such as wheat flour or rice flour, water and optionally salt. For leavened products, primarily baker's yeast is used, and optionally chemical leavening compounds can be used, such as a combination of an acid (generating compound) and bicarbonate. Cereals from which flour can be made include maize, rice, wheat, barley, sorghum, millet, oats, rye, triticale, buckwheat, *quinoa*, spelt, einkorn, emmer, durum and kamut The term dough herein also includes a batter. A batter is a semi-liquid mixture, being thin enough to drop or pour from a spoon, of one or more flours combined with liquids such as water, milk or eggs used to prepare various foods, including cake.

The term "pre-mix" is to be understood in its conventional meaning, i.e. as a mix of baking agents, generally including flour, starch, maltodextrin and/or salt, which may be used not only in industrial bread-baking plants/facilities, but also in retail bakeries. A pre-mix comprises a polypeptide having lipase activity as disclosed herein. A pre-mix may contain additives as mentioned herein.

Additives are in most cases added in powder form. Suitable additives include oxidants (including ascorbic acid, bromate and azodicarbonamide (ADA), reducing agents (including L-cysteine), emulsifiers (including without limitation mono- and diglycerides, monoglycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), propylene glycol monostearate (PGMS), lecithin), gums (including guar gum and xanthan gum), flavours, acids (including citric acid, propionic acid), starches, modified starches, humectants (including glycerol) and preservatives.

The term "control sequence" as used herein refers to components involved in the regulation of the expression of a coding sequence in a specific organism or in vitro. Examples of control sequences are transcription initiation sequences, termination sequences, promoters, leaders, signal peptides, propeptides, prepropeptides, or enhancer sequences; Shine-Delgarno sequences, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion.

The term "expression" includes any step involved in the production of the polypeptide including, but not limited to, transcription, post transcriptional modification, translation, post-translational modification, and secretion.

An expression vector comprises a polynucleotide coding for a polypeptide, operably linked to the appropriate control sequences (such as a promoter, and transcriptional and translational stop signals) for expression and/or translation in vitro. The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector, which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon. Vectors preferred for use in bacteria are for example disclosed in WO-A1-2004/074468.

A host cell as defined herein is an organism suitable for genetic manipulation and one which may be cultured at cell densities useful for industrial production of a target product, such as a polypeptide according to the present invention. A host cell may be a host cell found in nature or a host cell derived from a parent host cell after genetic manipulation or classical mutagenesis. Advantageously, a host cell is a recombinant host cell. A host cell may be a prokaryotic, archaebacterial or eukaryotic host cell. A prokaryotic host cell may be, but is not limited to, a bacterial host cell. An eukaryotic host cell may be, but is not limited to, a yeast, a fungus, an amoeba, an algae, a plant, an animal, or an insect host cell.

A nucleic acid or polynucleotide sequence is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein. A nucleic acid or polynucleotide sequence is defined herein as a nucleotide polymer comprising at least 5 nucleotide or nucleic acid units. A nucleotide or nucleic acid refers to RNA and DNA.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in the presence of a specific substrate under certain conditions may be referred to as enzymes. It will be understood that, because of the degeneracy of the genetic code, a multitude of nucleotide sequences encoding a given polypeptide may be produced.

A polypeptide as disclosed herein may be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the host cell. Examples of fusion polypeptides and signal sequence fusions are for example as described in WO2010/121933.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 80% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

A "mature polypeptide" is defined herein as a polypeptide in its final form and is obtained after translation of a mRNA into polypeptide and post-translational modifications of said polypeptide. Post-translational modifications include N-terminal processing, C-terminal truncation, glycosylation, phosphorylation and removal of leader sequences such as signal peptides, propeptides and/or prepropeptides by cleavage.

A "mature polypeptide coding sequence" means a polynucleotide that encodes a mature polypeptide.

The term "promoter" is defined herein as a DNA sequence that binds RNA polymerase and directs the polymerase to the correct downstream transcriptional start site of a nucleic acid sequence to initiate transcription. Suitable bacterial promotors are for instance disclosed in in WO-A1-2004/074468.

The term "recombinant" when used with reference to a nucleic acid or protein indicates that the nucleic acid or protein has been modified in its sequence if compared to its native form by human intervention. The term "recombinant" when referring to a cell, such as a host cell, indicates that the genome of the cell has been modified in its sequence if compared to its native form by human intervention. The term "recombinant" is synonymous with "genetically modified".

Sequence identity, or sequence homology are used interchangeable herein. To determine the percentage of sequence homology or sequence identity of two amino acid sequences or of two nucleic acid sequences, the sequences are aligned for optimal comparison purposes. To optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp276-277). For protein sequences EBLOSUM62 is used for the substitution matrix. For nucleotide sequences, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms. After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., XBLAST and NBLAST) can be used. See the homepage of the National Center for Biotechnology Information.

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 2, but still encoding the polypeptide according to the invention.

As used herein, the terms "variant" or "mutant" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

DETAILED DESCRIPTION

The present invention relates to a variant polypeptide having a lipase activity, wherein the polypeptide is selected from the group consisting of:
i. a polypeptide which comprises an amino acid sequence which has at least 70% identity to a mature amino acid sequence of SEQ ID NO: 1 or SEQ ID NO: 6, wherein the polypeptide comprises an amino acid substitution at position 295 and at least one further amino acid substitution at position 113, 121, 179 and/or 284, wherein the positions are defined with reference to SEQ ID NO: 1 or SEQ ID NO: 6,
ii. a polypeptide according to i), wherein the amino acid substitution at position 295 is D295G, D295N or D295S and the at least one further amino acid substitution at position 113 is I113H, I113N or I113T, at position 121 the amino acid substitution is N121D, at position 179 the amino acid substitution is V179M, and/or at position 284 the amino acid substitution is I284M or I284T; and
iii. a polypeptide which comprises an amino acid sequence which has at least 70% identity to a mature amino acid sequence of SEQ ID NO: 1 or SEQ ID NO: 6, wherein the polypeptide comprises amino acid substitutions (D295S and V179M), (D295N and V179M), (D295S, I113H and V179M), (D295G and I113T), (D295N and I113N), (D295N, I113T, V179M, and N112D), (D295S, I113H, V179M, and I284M), (D295N and (I113T), (D295S, I113T, V179M, and I284M), (D295S, I113T, V179M, N121D), (D295S, I113T and V179M), (D295S and I113N), or (D295N and I284T), wherein the substitutions are defined with reference to SEQ ID NO: 1, or SEQ ID NO: 6; and,
iv. a polypeptide according to i)-iii), wherein the polypeptide comprises an insertion of one or more amino acids after position 304, wherein the position is defined with reference to SEQ ID NO: 1 or SEQ ID NO: 6; and,
v. a polypeptide according to iv), wherein the mature amino acid sequence comprises the insertion.

Accordingly, the present invention relates to a variant polypeptide having a lipase activity, wherein the polypeptide is selected from the group consisting of:
i. a polypeptide which comprises an amino acid sequence which has at least 70% identity to a mature amino acid sequence of SEQ ID NO: 1, wherein the polypeptide comprises an amino acid substitution at position 295 and at least one further amino acid substitution at position 113, 121, 179 and/or 284, wherein the positions are defined with reference to SEQ ID NO: 1;
ii. a polypeptide according to i), wherein the amino acid substitution at position 295 is D295G, D295N or D295S and the at least one further amino acid substitution at position 113 is I113H, I113N or I113T, at position 121 the amino acid substitution is N121D, at position 179 the amino acid substitution is V179M, and/or at position 284 the amino acid substitution is I284M or I284T; and
iii. a polypeptide which comprises an amino acid sequence which has at least 70% identity to a mature amino acid sequence of SEQ ID NO: 1, wherein the polypeptide comprises amino acid substitutions (D295S and V179M), (D295N and V179M), (D295S, I113H and V179M), (D295G and I113T), (D295N and I113N), (D295N, I113T, V179M, and N112D), (D295S, I113H, V179M, and I284M), (D295N and I113T), (D295S, I113T, V179M, and I284M), (D295S, I113T, V179M, N121D), (D295S, I113T and V179M), (D295S and I113N), or (D295N and I284T), wherein the substitutions are defined with reference to SEQ ID NO: 1; and, iv. a polypeptide according to i)-iii), wherein the polypeptide comprises an insertion of one or more amino acids after position 304, wherein the position is defined with reference to SEQ ID NO: 1, and v. a polypeptide according to iv), wherein the mature amino acid sequence comprises the insertion Accordingly, the present invention also relates to a variant polypeptide having a lipase activity, wherein the polypeptide is selected from the group consisting of:

i. a polypeptide which comprises an amino acid sequence which has at least 70% identity to a mature amino acid sequence of SEQ ID NO. 6, wherein the polypeptide comprises an amino acid substitution at position 295 and at least one further amino acid substitution at position 113, 121, 179 and/or 284, wherein the positions are defined with reference to SEQ ID NO: 6;

ii. a polypeptide according to i), wherein the amino acid substitution at position 295 is D295G, D295N or D295S and the at least one further amino acid substitution at position 113 is I113H, I113N or I113T, at position 121 the amino acid substitution is N121D, at position 179 the amino acid substitution is V179M, and/or at position 284 the amino acid substitution is I284M or I284T; and iii. a polypeptide which comprises an amino acid sequence which has at least 70% identity to a mature amino acid sequence of SEQ ID NO: 6, wherein the polypeptide comprises amino acid substitutions (D295S and V179M), (D295N and V179M), (D295S, I113H and V179M), (D295G and I113T), (D295N and I113N), (D295N, I113T, V179M, and N112D), (D295S, I113H, V179M, and I284M), (D295N and I113T), (D295S, I113T, V179M, and I284M), (D295S, I113T, V179M, N121D), (D295S, I113T and V179M), (D295S and I113N), or (D295N and I284T), wherein the substitutions are defined with reference to SEQ ID NO: 6; and iv. a polypeptide according to i)-iii), wherein the polypeptide comprises an insertion of one or more amino acids after position 304, wherein the position is defined with reference to SEQ ID NO: 6, and v. a polypeptide according to v), wherein the mature amino acid sequence comprises the insertion Surprisingly, it was found that when using a polypeptide as disclosed herein in a dough, the shock resistance was increased, the dough stability was improved and/or the volume of a baked product made from the dough was increased as compared to the shock resistance, the dough stability and/or volume of a baked product made from a dough comprising a reference polypeptide. A reference polypeptide may be defined as a parent polypeptide of the variant polypeptide as disclosed herein. The wording reference and parent polypeptide are used interchangeable herein. A reference polypeptide as disclosed herein may be a polypeptide comprising at least 70%, 75%, 80%, 85%, 90% or 95% or 100% identity to the mature amino acid sequence of SEQ ID NO: 1, but which does not comprise an amino acid substitution D295G, D295N or D295S, and does not contain or comprise at least one further amino acid substitution I113H, I113N or I113T, N121D, V179M, and/or I284M or I284T. A reference polypeptide as disclosed herein may also be a polypeptide comprising at least 70%, 75%, 80%, 85%, 90% or 95% or 100% identity to the mature amino acid sequence of SEQ ID NO: 6, but which does not contain or comprise an amino acid substitution D295G, D295N or D295S, and does not contain or comprise at least one further amino acid substitution I113H, I113N or I113T, N121D, V179M, and/or I284M or I284T.

A reference or parent polypeptide may comprise or contain amino acids 34 to 304 of SEQ ID NO: 1 or amino acids 34 to 304 of SEQ ID NO: 6.

A baked product as used herein may be a bread. The improved dough stability and/or increased volume of the baked product was surprisingly found in a dough and a baked product comprising wholemeal flour and/or a flour comprising 0.01 to 0.8 w/w %, for instance 0.05 to 0.6 w/w %, for instance 0.1 w/w % to 0.5 w/w % or 0.2 to 4 w/w % free fatty acids. Fatty acids in grains or cereals are known and comprise palmitic acid, oleic acid, linoleic acid and/or linolenic acid. Flour may be a flour that has been stored, for instance stored for 1 day to 10 years, for instance for 1 month to 5 years, or stored for 2 months to 1 year Dough stability can be determined by measuring the volume of a baked product made from the dough. The volume of a baked product prepared from a dough comprising a polypeptide as disclosed herein was increased by 1 to 40%, for instance 2 to 30%, for instance by 3 to 20% for instance by 4 to 15%, compared to the volume of a baked product prepared from a dough comprising a reference polypeptide having lipase activity. The increased volume of a baked product prepared from a dough comprising a polypeptide as disclosed herein may be determined after a shock treatment of the dough as defined herein.

A polypeptide having a lipase activity as disclosed herein may be a polypeptide which comprises an amino acid sequence which has at least 60%, 70%, 75%, 80%, 85%, 90%, 91%, 92%, 93%, 94%, 95%, 96%, 97%, 98% or at least 99% identity to a mature amino acid sequence of SEQ ID NO: 1, or SEQ ID NO: 6, wherein the polypeptide comprises an amino acid substitution at position 295 and at least one further amino acid substitution at position 113, 121, 179 and/or 284, wherein the positions are defined with reference to SEQ ID NO: 1 or SEQ ID NO:6.

A polypeptide having a lipase activity as disclosed herein may be a polypeptide which comprises an amino acid sequence which has at least 60%, 70%, 75%, 80%, 85%, 90%, 91%, 92%, 93%, 94%, 95%, 96%, 97%, 98% or at least 99% identity to a mature amino acid sequence of SEQ ID NO: 1 or SEQ ID NO: 6, wherein the polypeptide comprises amino acid substitutions (D295S and V179M), (D295N and V179M), (D295S, I113H and V179M), (D295G and I113T), (D295N and I113N), (D295N, I113T, V179M, and N112D), (D295S, I113H, V179M, and I284M), (D295N and I113T), (D295S, I113T, V179M, and I284M), (D295S, I113T, V179M, N121D), (D295S, I113T and V179M), (D295S and I113N), or (D295N and I284T), wherein the substitutions are defined with reference to SEQ ID NO: 1 or SEQ ID NO: 6.

A polypeptide as disclosed herein may be an isolated or a synthetic polypeptide.

A variant polypeptide having a lipase activity as disclosed herein may comprise one or more further amino acid substitutions. For instance, a polypeptide having lipase activity as disclosed herein may comprise 1, 2, 3, 4, 5, 6, 7, 8, 9, 10, 11 or 12 or more further amino acid substitutions, deletions and/or insertions, whereby the polypeptide still has the activity or function of the polypeptide of the invention.

The amino acids are referred herein with their single letter code known to a person skilled in the art and can be found in Sambrook & Russell, *Molecular Cloning: A Laboratory Manual*, 3rd Ed., CSHL Press, Cold Spring Harbor, NY, 2001. To exemplify, the amino acids at the positions identified herein are D=Asp=aspartic acid, G=Gly=Glycine, N=Asn=Asparagine, I=Ile=Isoleucine; H=His=Histidine; V=Val=Valine; M=Met=Methionine; P=Pro=Proline; S=Ser=Serine; T=Thr=Threonine.

A polypeptide having a lipase activity is also referred to as a lipase or a lipolytic enzyme. A polypeptide having a lipase activity as disclosed herein may have any suitable lipase activity, such as triacylglycerol lipase, galactolipase, and/or phospholipase activity. A lipase as disclosed herein may have a phospholipase A1 activity. Lipase activities may be determined according to known methods in the art A triacyiglycerol-lipase (EC 3.1.1.3) hydrolyses an ester bond in triglycerides (also known as triacylglycerol or triacyl glycerides (TAG)).

A galactolipase (EC 3.1.1.26) hydrolyses an ester bond in galactolipids. Galactolipids consist of a glycerol backbone with esterified fatty acid, while the second and/or third hydroxyl group is bound to sugar residues such as in case of galactolipids a galactose, for example monogalactosyl-diglyceride (MGDG) or digalactosyldiglyceride (DGDG).

A phospholipase A1 (EC 3.1.1.32) catalyses the diacylation of a fatty acyl group at the sn-1 position from a phospholipid (diacyl glycerophospholipid) to produce a lysophospholipid and a free fatty acid.

A variant polypeptide having a lipase activity comprising the amino acid substitutions as disclosed herein comprises at least 70% identity to a mature amino acid sequence of SEQ ID NO: 1 or SEQ ID NO: 6. The mature amino acid sequence of SEQ ID NO: 1 may comprise or contain amino acids 34 to 304 of SEQ ID NO: 1, amino acids 34 to 302, amino acids 34 to 303, amino acids 34 to 307, amino acids 31 to 303, amino acids 31 to 304 and/or amino acids 31 to 307. The mature amino acid sequence of SEQ ID NO: 1 may comprise or contain amino acids 34 to 304 of SEQ ID NO: 1. The length of a polypeptide having lipase activity, such as the length of a mature amino acid sequence of SEQ ID NO: 1 may be determined by LC-MS analysis as disclosed in the materials and methods section.

The mature amino acid sequence of SEQ ID NO: 6 comprises or contains amino acids 34 to 304 of SEQ ID NO:6.

A polypeptide as disclosed herein may comprise an insertion of one or more amino acids after position 304, wherein the position is defined with reference to SEQ ID NO: 1 or SEQ ID NO: 6. Accordingly, between position 304 and 305 of SEQ ID NO: 1 or SEQ ID NO: 6 one or more amino acid(s), for instance two amino acids are inserted. Any suitable amino acid may be inserted between position 304 and 305. The insertion after position 304 of SEQ ID NO: 1 or SEQ ID NO: 6 may comprise two amino acids of proline (proline (P)-proline (P)).

In one embodiment the mature amino acid sequence of polypeptide as defined herein may comprise the insertion. For instance, a polypeptide having a lipase activity as defined herein comprising any of the amino acid substitutions as disclosed herein may be a polypeptide which has at least 70%, 75%, 80%, 85%, 90%, 91%, 92%, 93%, 94%, 95%, 96%, 97%, 98% or at least 99% identity to the mature amino acid sequence of SEQ ID NO: 3. A mature amino acid sequence of SEQ ID NO: 3 comprises amino acids 34 to 306 of SEQ ID NO: 3.

The present invention also relates to a nucleic acid encoding a polypeptide having lipase activity as disclosed herein. The nucleic acid may be a nucleic acid which has at least 60%, 70%, 75%, 80% 85%, 90%, 91%, 92%, 93%, 94%, 95%, 96%, 97%, 98%, or 99% identity to SEQ ID NO: 2 or SEQ ID NO: 4, or SEQ ID NO: 7, wherein the nucleic acid comprises a mutation encoding an amino acid substitution D295G, D295N or D295S and at least one further amino acid substitution at position I113H, I113N or I113T, and/or N121D, and/or V179M, and/or I284M or I284T wherein the amino acid substitutions are defined with reference to SEQ ID NO: 1 or SEQ ID NO: 6. The nucleic acid as disclosed herein may be a nucleic acid which has at least 60%, 70%, 75%, 80% 85%, 90%, 91%, 92%, 93%, 94%, 95%, 96%, 97%, 98%, or 99% identity to SEQ ID NO: 2, SEQ ID NO: 4 or SEQ ID NO: 7, wherein the nucleic acid comprises a mutation encoding the amino acid substitutions (D295S and V179M), (D295N and V179M), (D295S, I113H and V179M), (D295G and I113T), (D295N and I113N), (D295N, I113T, V179M, and N112D), (D295S, I113H, V179M, and (I284M), (D295N and I113T), (D295S, I113T, V179M, and I284M), (D295S, I113T, V179M, N121D), (D295S, I113T and V179M), (D295S and I113N), or (D295N and I284T), wherein the substitutions are defined with reference to SEQ ID NO: 1 or SEQ ID NO:6.

A nucleic acid as disclosed herein may be an isolated or a synthetic nucleic acid.

Also disclosed herein is an expression vector comprising a nucleic acid as disclosed herein operably linked to at least one control sequence that directs expression of the polypeptide in a host cell.

There are several ways of inserting a nucleic acid into a nucleic acid construct or an expression vector which are known to a person skilled in the art, see for instance Sambrook & Russell, *Molecular Cloning: A Laboratory Manual*, 3rd Ed., CSHL Press, Cold Spring Harbor, NY, 2001. It may be desirable to manipulate a nucleic acid encoding a polypeptide of the present invention with control sequences, such as promoter and terminator sequences.

A variety of promoters can be used that can direct transcription in the host cells of the disclosure. A promoter sequence may be derived from a highly expressed gene. Strong constitutive promoters are well known and an appropriate one may be selected according to the specific sequence to be controlled in the host cell. Examples of suitable promotors are listed in WO 2009/106575, including examples of suitable promoters in filamentous fungi. All of the promoters mentioned therein are readily available in the art Any terminator which is functional in a cell as disclosed herein may be used, which are known to a person skilled in the art. Examples of suitable terminator sequences in filamentous fungi include terminator sequences of a filamentous fungal gene, for example those listed in WO 2009/106575.

Also disclosed herein is a recombinant host cell comprising a nucleic acid as disclosed herein, or an expression vector as disclosed herein.

A host cell may be a prokaryotic, archaebacterial or eukaryotic host cell. A prokaryotic host cell may be a bacterial host cell. A eukaryotic host cell may be a yeast, a fungus, an amoeba, an alga, a plant, an animal cell, such as a mammalian or an insect cell.

A eukaryotic cell may be a fungal cell, for example a yeast cell, such as a cell of the genus *Candida, Hansenula,*

*Kluyveromyces, Pichia, Saccharomyces, Schizosaccharomyces,* or *Yarrowia*. A yeast cell may be from *Kluyveromyces lactis, Saccharomyces cerevisiae, Hansenula polymorpha, Yarrowia lipolytica* and *Pichia pastoris, Candida krusei.*

Preferred filamentous fungal cells belong to species of an *Acremonium. Aspergillus, Chrysosporium, Myceliophthora, Penicillium, Talaromyces, Rasamsonia, Thielavia, Fusarium* or *Trichoderma* genus, and for instance a species of *Aspergillus niger, Aspergillus oryzae, Aspergillus awamori. Aspergillus foetidus, Aspergillus sojae, Aspergillus fumigatus, Acremonium alabamense Talaromyces emersonii, Rasamsonia emersonii, Chrysosporium lucknowense, Fusarium oxysporum, Myceliophthora thermophila, Trichoderma reesei, Thielavia terrestris* or *Penicillium chrysogenum*. A filamentous fungal host cell belongs to the genus *Aspergillus*, for instance the species *Aspergillus niger.*

A filamentous fungal cell may further comprise one or more modifications, preferably in its genome, such that the mutant filamentous fungal host cell is deficient in the cell in at least one product selected from glucoamylase (glaA), acid stable alpha-amylase (amyA), neutral alpha-amylase (amyBI and amyBII-WO2011009700), an α-1,3-glucan synthase (preferably AgsE or AgsE and AgsA, WO2014013074, WO2016066690), α-amylase AmyC (AmyC), a toxin, preferably ochratoxin and/or fumonisin (WO2011009700), a protease transcriptional regulator prtT (WO 00/20596, WO 01/68864, WO 2006/040312 and WO 2007/062936), PepA, a product encoded by the gene hdfA and/or hdfB, a non-ribosomal peptide synthase npsE (WO2012001169), a zinc binuclear cluster transcriptional regulator-deficient strain (WO2018166943 and references therein) if compared to a parent host cell and measured under the same conditions.

Also disclosed herein is a method for generating a variant polypeptide, wherein the method comprises
 i. selecting a parent polypeptide which comprises an amino acid sequence which has at least 60%, 70%, 75%, 80% 85%, 90%, 91%, 92%, 93%, 94%, 95%, 96%, 97%, 98%, or 99% identity to SEQ ID NO: 1 or SEQ ID NO: 6 or to a mature amino acid sequence of SEQ ID NO: 1 or SEQ ID NO: 6; and
 ii. substituting an amino acid at position 295 into G, N or S and substituting at least one further amino acid at position 113 into H, N or, T; and/or at position 121 into D; and/or at position 179 into M, and/or at position 284 into M or T, wherein the positions are defined with reference to SEQ ID NO: 1 or SEQ ID NO: 6.

Generating a variant polypeptide as disclosed herein may include expressing a gene encoding the variant polypeptide in a suitable recombinant host cell and cultivating the host cell to generate the variant polypeptide.

The present disclosure also relates to a method for the preparation of a polypeptide as disclosed herein, comprising cultivating a host cell as disclosed herein in a suitable fermentation medium, under conditions that allow expression of the polypeptide, and optionally recovering the polypeptide. A person skilled in the art knows how to perform a process for preparing a polypeptide having lipase activity depending on the host cell used. A suitable fermentation medium usually comprises a carbon and nitrogen source. Usually a fermentation medium has a pH value of between 3 and 8. A suitable temperature at which a host cell is cultivated is usually between 25 and 60° C. Host cells can be cultivated in shake flasks, or in fermenters having a volume of 0.5 or 1 litre or larger up to 10 to 100 or more cubic metres. Cultivation may be performed aerobically or anaerobically depending on the requirements of a host cell.

Advantageously a polypeptide as disclosed herein is recovered or isolated from the fermentation medium. Recovering or isolating a polypeptide from a fermentation medium may for instance be performed by centrifugation, filtration, and/or ultrafiltration.

The present invention also relates to a composition comprising a polypeptide according to the present invention. A composition may be a solid or fluid composition. A composition may comprise one or more components selected from the group consisting of milk powder, gluten, granulated fat, an additional enzyme, an amino acid, a salt, an oxidant, a reducing agent, an emulsifier, sodium stearoyl lactylate, calcium stearoyl lactylate, polyglycerol esters of fatty acids and diacetyl tartaric acid esters of mono- and diglycerides, a gum, a flavour, an acid, a starch, a modified starch, a humectant and a preservative. A composition includes a pre-mix.

A composition as disclosed herein may comprise one or more further enzyme(s) such as an amylase such as an alpha-amylase, for example a fungal alpha-amylase (which may be useful for providing sugars fermentable by yeast), a beta-amylase; a glucanotransferase, a peptidase in particular, an exopeptidase (which may be useful in flavour enhancement); a transglutaminase; a cellulase; a hemicellulase, in particular a pentosanase such as xylanase (which may be useful for the partial hydrolysis of pentosans, more specifically arabinoxylan, which increases the extensibility of the dough); protease (which may be useful for gluten weakening in particular when using hard wheat flour), a protein disulfide isomerase, e.g., a protein disulfide isomerase as disclosed in WO 95/00636; a glycosyltransferase; a peroxidase (which may be useful for improving the dough consistency); a laccase; an oxidase, such as an hexose oxidase, a glucose oxidase, aldose oxidase, pyranose oxidase; a lipoxygenase; L-amino acid oxidase (which may be useful in improving dough consistency) and/or an asparaginase.

The present invention also relates to a process for preparing a dough comprising adding a polypeptide as disclosed herein or a composition as disclosed herein to the dough. A process for preparing a dough is known to a person skilled in the art and usually comprises mixing dough ingredients such as flour, water, and optionally salt. A process for preparing a dough as disclosed herein comprises adding a polypeptide having lipolytic activity to the dough, for instance during preparation of the dough, for instance during mixing other dough ingredients. A suitable amount of a polypeptide having lipolytic activity is added to the dough. A suitable amount of a polypeptide having lipolytic activity may for instance be expressed in GalLU.

A suitable amount of a polypeptide having lipase activity may be from 10 to 3000 GalLU per kg flour, for instance from 20 to 2000 GalLU per kg flour, for instance from 50 to 1500 GalLU per kg flour, for instance from 100 to 1400 GalLU per kg flour.

The present invention also relates to a dough comprising a variant polypeptide as disclosed herein or a composition as disclosed herein. Surprisingly, it was found that a dough or a baked product made from the dough as disclosed herein has an improved property as compared to a dough prepared with a reference polypeptide. In particular, the improved property was found when the dough was made from wholemeal flour and/or a flour comprising a free fatty acid content of from 0.01 to 0.8 w/w % for instance from 0.05 to 0.6 w/w % for instance from 0.1 to 0.5 w/w %. The free fatty acids in a flour may be originally present or formed upon storage of the flour. An improved property may be an increased shock resistance, increased stability of the dough and/or an improved bread volume. A reference polypeptide is a polypeptide as defined herein above.

The term "increased stability of the dough" is defined herein as the property of a dough that is less susceptible to forming faults as a consequence of mechanical abuse, and thus better at maintaining its shape and volume as compared to a reference dough. Dough stability can be evaluated by the ratio of height:width of a cross section of a loaf after normal and/or extended proof.

An improved dough stability may be an improved shock resistance of a dough. Improved shock resistance of a dough may be demonstrated by subjecting the dough to a shock treatment as follows.

After proofing, doughs in their respective tins are subjected to mechanical jarring by a 250 g metal ball, rolling down a track set at around 45° using bespoke apparatus, running into the tins containing the doughs; for a so-called 'medium shock', the track was set at height of around 350 mm, such as 310 mm, while for a so-called 'high shock', the track was set at a height of around 650 mm, such as 600 mm.

The term "increased volume of the baked product" is preferably measured as the volume of a given loaf of bread determined by an automated bread volume analyser (e.g. BVM-3, Tex Vol Instruments AB, Viken, Sweden), using ultrasound or laser detection as known in the art and compared to the volume of a reference baked product. In case the volume is increased, the property is improved. Alternatively, the height of the baked product after baking in the same size tin is an indication of the baked product volume. In case the height of the baked product has increased, the volume of the baked product has increased.

The present invention also relates to a process for preparing a baked product comprising baking a dough as disclosed herein. A person skilled in the art knows how to prepare a baked product, and usually comprises baking a dough in an oven at a suitable temperature to prepare the baked product. Suitable temperatures for preparing a baked product are for instance between 100° C. and 300° C.

The present invention also relates to the use of a variant polypeptide as disclosed herein to increase the shock resistance of a dough, or improve stability of a dough, or increase the volume of a bread made from the dough. Accordingly, disclosed herein is a method for improving the shock resistance of a dough or improving the stability of dough, using a polypeptide as disclosed herein. The use of a variant polypeptide as disclosed herein to increase shock resistance of a dough, improve stability or a dough, and/or increase volume of a baked product as disclosed herein is relative to the use of a reference polypeptide as defined herein above. Accordingly, disclosed herein is a method for increasing the shock resistance of a dough, improve the stability of a dough and/or improving the volume of a baked product using a polypeptide as disclosed herein.

The present invention also relates to a process for increasing the volume of a baked product, comprising
preparing a dough comprising a polypeptide as disclosed herein
subjecting the dough to a shock treatment, and
baking the dough,
wherein the volume of the baked product is increased as compared to the volume of a baked product prepared from a dough comprising a reference polypeptide as defined herein above.

A dough or a baked product disclosed herein may comprise any suitable cereal flour, for instance wholemeal flour, or a mixture of different flours. Cereal flour may also comprise bran, grains and/or seeds. Cereals include maize, rice, wheat, barley, sorghum, millet, oats, rye, triticale, buckwheat, *quinoa*, spelt, einkorn, emmer, durum and kamut. Wholemeal flour, also referred to as whole-wheat flour, is flour made from the entire wheat kernel or grain including the outer part. Flour may comprise a free fatty acid content of between 0.01 to 0.8 w/w %, for instance 0.05 to 0.6 w/w %, for instance a free fatty acid content of between 0.1 to 0.5 w/w % or between 0.14 to 0.4 w/w %. During storage the content of free fatty acids in flour usually increases. Free fatty acids may for instance be linoleic acid (C18:2), palmitic acid (C16:0), oleic acid (C18:1), linolenic acid (C18:3) (see for instance MacMurray and Morrison, J. Sci. Food Agr. 21:520-528 (1970). Free fatty acids in flour may be determined by methods known to a person skilled in the art, for instance as disclosed in Fierens et al, J. of Cereal Science 65 (2015), p. 81-87.

EXAMPLES

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology". Green Publishing and Wiley Interscience, New York (1987). Methods for transformation, genetic modification etc of fungal host cells are known from e.g. EP-A-0 635 574. WO 98/46772, WO 99/60102 and WO 00/37671, WO90/14423, EP-A-0481008, EP-A-0635 574 and U.S. Pat. No. 6,265,186.

Materials and Methods

GalLU Assay for Lipolytic Activity on DGDG at pH 5.5
The following solutions were prepared
1) Substrate solution: 1 g digalactosyldiglyceride (DGDG) from oat in 2% triton X-100 solution
2) 0.2 M acetate buffer pH 5.5
3) 0.1 M $CaCl_2$)
4) Stop solution: 1 M HCl A mixture of 500 µL solution 1, 250 µL solution 2 and 50 µL solution 3 was equilibrated at 37° C. The reaction was started by adding 100 µL of a solution contain lipolytic activity (suitably diluted to contain an activity between 0.05-1.0 GalLU/mL). After 10 min incubation at 37° C. the reaction was stopped by adding 100 µL solution 4. A blank measurement was performed by incubating a mixture of 500 µL solution 1, 250 µL solution 2 and 50 µL solution 3 without sample containing lipolytic activity for 10 minutes at 37° C. After adding 100 µL of solution 4 (stop solution). 100 µL solution containing lipolytic activity was added. The amount of free fatty acid formed in reaction and blank was determined by following the instructions described in the package insert of the Wako HR series NEFA-HR (2) diagnostic kit (Cat. No. 999-34691/991-34891/993-35191). Activity is calculated as follows:
GalLU/mL=(ΔFFA×Vt×df)/(Vs×t)
ΔFFA=FFA in sample−FFA in blank (µmol/mL)
Vt=total volume after stopping the reaction (1 mL)
Vs=sample volume (0.1 mL)
t=incubation time (10 minutes)
df=dilution factor of sample
1 GalLU is defined as the amount of enzyme that liberates one micromole of free fatty acid per minute under the conditions of the test.

LC-MS Analysis

Before LC-MS analysis the protein samples are trichloroacetic acid (TCA) precipitated by adding TCA to a final concentration of 10%. After centrifugation the precipitate was washed with acetone, and subsequently dissolved in 50 mM sodium hydroxide, and further diluted with 100 mM ammonium bicarbonate, prior to deglycosylation with PNGase F. For the characterization of the intact protein mass amino acid backbone by LC-MS all samples were analyzed with an Acquity I-class-Synapt G2-S (Waters), which was operated in positive Electrospray ionization mode (ESI-pos), used in resolution mode (R=20000 FWHM), and scanning from 500-3500 m/z.

The chromatographic separation was achieved with a Waters Acquity UPLC Protein BEH300 C4 1.7 μm 300A pore size 2.1×50 mm column, using a gradient elution with (A) 0.1% Formic acid (FA) in LC-MS grade water, and B) 0.1% FA in acetonitrile LC-MS grade, as mobile phases. The 15-minute gradient started with 2% B, and after 2 minutes then linearly increased to 15% B in 0.2 minutes, then linearly increased to 40% B for 5.8 minutes, followed by a linear increase to 95% B in 0.2 minutes and kept there for 4 minutes, then re-equilibrating with 2% B for 4 min. The flow rate was kept at 0.4 ml/min, using an injection volume of 2 μL and the column temperature was set to 75° C. Deconvolution of the ESI-pos spectra was performed with Waters MaxEnt1 software to convergence, resulting in the average molecular weight (MW) of proteins, within ~50 ppm of the theoretical MW.

Strains
- WT 1: This *Aspergillus niger* strain is used as a wild-type strain. This strain is deposited at the CBS Institute under the deposit number CBS 513.88.
- GBA 306: The construction of GBA 306 using WT1 as starting strain has been described in detail in WO2011/009700. This GBA 306 strain has the following genotype: ΔglaA, ΔpepA, ΔhdfA, an adapted BamHI amplicon, ΔamyBII, ΔamyBI, and ΔamyA.

Enzymes

Panamore® Golden was commercially available from DSM Food Specialties. Panamore® Golden comprises wild-type mature lipase from SEQ ID NO. 1.

Lipopan® F was obtained from Novozymes. Lipopan® F comprises wild-type mature lipase from SEQ ID NO: 6.

Example 1: Design, Cloning and Expression of a Lipolytic Enzyme Variant

Design and Cloning

The protein sequence (amino acid sequence) of the reference polypeptide (also referred to as parent (mature) polypeptide) having lipolytic activity is shown in amino acids 34 to 304 SEQ ID NO: 1. A codon-adapted DNA sequence for expression of the lipolytic enzyme proteins (lipolytic enzyme variants and reference polypeptide) in *Aspergillus niger* was designed containing additional BsaI type II restriction enzyme sites to enable subcloning in the *Aspergillus* expression vector pGBFIN-50 (see also FIG. 1). Codon adaptation was performed as described in WO2008/000632. The codon optimized DNA sequence for expression of the gene encoding the reference polypeptide of SEQ ID NO: 1 in *A. niger* is shown in SEQ ID NO: 2.

In addition, a polypeptide sequence having amino acids 34 to 304 of SEQ ID NO: 1 and an insertion of two prolines after position 304 was made, as shown in amino acids 34 to 306 of SEQ ID NO: 3. The codon optimized DNA sequence for expression of the gene encoding a polypeptide of SEQ ID NO: 3 in *A. niger* is shown in SEQ ID NO: 4.

In addition, a reference polypeptide having lipolytic activity having the mature amino acid sequence of SEQ ID NO: 6, i.e. amino acids 34 to 304 of SEQ ID NO: 6 was made in a similar way as described above. The codon optimized DNA sequence for expression of the gene encoding the reference polypeptide of SEQ ID NO: 6 in *A. niger* is shown in SEQ ID NO: 7.

Variant lipases of SEQ ID NO: 1 are indicated as PAN2 [ . . . ], variant lipases of SEQ ID NO: 3 are indicated as NBL [ . . . ] and variant lipases of SEQ ID NO: 6 are indicated as LPV [ . . . ] (see Tables 1 and 3).

Figure 2:
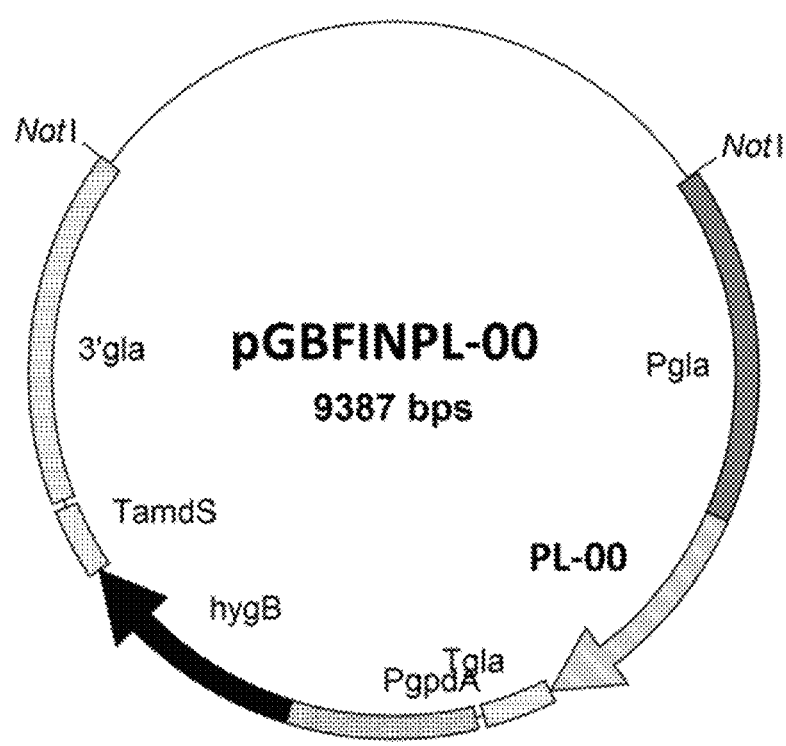
FIG. 2. Sets out the *Aspergillus* lipolytic enzyme expression vector pGBFINPL-00

The translational initiation sequence of the glucoamylase glaA promoter was modified into 5'-CACCGTCAAA ATG-3' (SEQ ID NO: 5) (already present in the *Aspergillus* expression vector pGBFIN-50) and an optimal translational termination sequence 5'-TAAA-3' was used in the generation of the lipolytic enzyme expression constructs (as also detailed in WO2006/077258 and WO2011/009700). The DNA sequences coding for the lipolytic enzyme variants and for the reference polypeptide of the invention were synthesized completely (ATUM/DNA2.0, Newark, USA) and cloned into *Aspergillus niger* expression vector pGBFIN-50 thru repetitive steps of BsaI digestion and ligation (Golden-Gate cloning method (New England Biolabs), according standard procedure. The resulting vectors containing the lipolytic enzyme variant expression cassette under control of the glucoamylase promoter were named pGBFINPL-00 #(see FIG. 2) encoding any of the variant polypeptides as disclosed in Table 1 and 3.

Subsequently, *A. niger* GBA 306 was transformed with a PCR-amplified Pgla-3'gla lipolytic expression cassette fragment generated using the respective pGBFINPL-00 #vectors as template. The PCR fragment comprises the lipolytic enzyme expression cassette under control of the glucoamylase promoter and terminator as well as the hygromycin selection marker. Alternatively, a NotI-digested and purified fragment of the vectors containing the lipolytic enzyme expression cassette and the hygromycin selection marker could have been used. Transformation experiments were performed with strain and methods as described in WO199846772, WO199932617, WO2011009700, WO2012001169, WO2013135729, WO2014013073 and WO2014013074 and references therein. After transformation, the protoplasts were plated onto selective regeneration medium consisting of *Aspergillus* minimal medium supplemented with 60 μg/ml. Hygromycin B. After incubation for 5-10 days at 30° C., single transformants were restreaked to single colonies on PDA (Potato Dextrose Agar) supplemented with 60 μg/mL Hygromycin B. After 5-7 days growth and sporulation at 30° C., single colonies were transferred to PDA plates. Following growth for 5-7 days at 30° C., spores were isolated and used as inoculation material for shake flask fermentations.

TABLE 1

Variant lipolytic enzymes with amino acid substitutions and insertions relative to SEQ ID NO: 1 (PAN[ . . . ] and NBL[ . . . ]) or SEQ ID NO: 6 (LPV[ . . . ])

| Variant No° | Variant name | Substitutions | Insertions |
| --- | --- | --- | --- |
| 1 | PAN2_R2_T1_13 | D295S; V179M | |
| 2 | PAN2_R2_T1_14 | D295N; V179M | |
| 3 | PAN2_R2_T1_33 | D295S; I113H; V179M | |
| 4 | PAN2_R2_T1_10 | D295N; I113T; V179M; N121D | |
| 5 | PAN2_R2_T1_57 | D295S; I113H; V179M; I284M | |
| 6 | PAN2_R2_T1_26 | D295N; I284T | |
| 7 | PAN2_R2_T1_53 | D295S; I113T; V179M; I284M | |
| 8 | PAN2_R2_T1_61 | D295S; I113T; V179M; N121D | |
| 9 | PAN2_R2_T1_29 | D295S; I113T; V179M; | |
| 10 | PAN2_R2_T3_85 | D295S; I113N | |
| 11 | NBL_R2_T1_25 | D295N; V179M | 305P + 306P |
| 12 | NBL_R2_T1_15 | D295G; I113T | 305P + 306P |
| 13 | NBL50_R2_T1-17 | D295N; I113N | 305P + 306P |
| 14 | NBL50_R2_T1-13 | D295N; I113T | 305P + 306P |
| 15 | NBL_R2_T1_37 | D295N; I284T | 305P + 306P |
| 16 | LPV01 | SEQ ID: 6 | |
| 17 | LPV02 | I113N; D295S | |
| 18 | LPV05 | I284T; D295N | 305P + 306P |
| 19 | LPV06 | I113T; D295G | |

Expression of the Lipolytic Enzyme Variants

Fresh *A. niger* spores containing the vectors as disclosed above were prepared and used for generating lipolytic enzyme sample material by cultivation of the strains in shake flask. *A. niger* strains were precultured in 20 mL preculture medium in a 100 mL shake flask with baffle containing per liter: 100 g Corn Steep Solids (Roquette), 1 g NaH2PO4·H2O, 0.5 g MgSO4.7H2O, 10 g Glucose·H2O, 0.25 g Basildon pH5.8. After overnight growth at 34° C. and 170 rpm 10 mL of this culture was transferred to 100 mL fermentation medium in 500 mL shake flasks with baffle. Fermentation medium contains per liter: (150 g maltose, 60 g bacto-soytone, 15 g (NH4)2SO4, 1 g NaH2PO4·H2O, 1 g MgSO4·7H2O, 1 g L-arginine, 0.08 g Tween-80, 0.02 g Basildon, 20 g MES, pH 6.2 Cultures were grown for 2-7 days at 34° C., 170 rpm. Culture supernatants were recovered by centrifugation for 10 min at 5000×g. The lipase activity (GalLU) in the supernatants was determined as disclosed above and shown in Table 3.

Example 2: Effect of a Variant Lipases of SEQ ID NO: 1 and SEQ ID NO: 3 on the Volume of a Wholemeal Baked Product A wholemeal flour stress-test was carried out with recipe and process conditions as shown in Table 2.

Wholemeal flour (*acasia*) was from Meneba, compressed yeast (Koningsgist) was from AB Mauri, Amylase Bakezyme® P500 and xylanase Bakezyme® HSP6000 were from DSM Food Specialties, the vital wheat gluten (Amygluten 110) from Syral, and other materials from general bakery suppliers. Addition of materials was by bakers' percent, or ppm, that is on a flour weight basis. Lipase was mixed together with the other ingredients. The amount and effect of variant lipase as disclosed in Table 1 was assessed against an optimal dose of Panamore® Golden of 20 ppm for this application, using dose ranges of the variants to determine optimal use levels for these. The amount of variant lipase that resulted in the maximum volume of bread, the optimal dose, was used in the present baking trial.

Dough was prepared from batches of 2 kg of flour, to form at least 6×350 g dough pieces after moulding which were placed in appropriate baking-tins (187 mm×96 mm×96 mm). After proofing, at least 4 doughs in their respective tins were subjected to mechanical jarring by a 250 g metal ball, rolling down a track set at around 45° using bespoke apparatus, running into the tins containing the doughs. For a so-called 'medium shock', the track was set at height of around 310 mm, while for a so-called 'high shock', the track was set at a height of around 600 mm. At least 2 dough

TABLE 2

Process conditions wholemeal stress test

| Formulation: | | Process: | |
| --- | --- | --- | --- |
| Compressed Yeast | 5% | Diosna SP12 mixer | 600 turns 25 Hz + 40 Wh/kg 50 Hz |
| Ascorbic Acid | 20 ppm | Dough temp after mix | 27-29° C. |
| Amylase, Bakezyme P500 | 5 ppm | Rest/bench time | 10 min |
| Xylanase, Bakezyme HSP6000 | 15 ppm | Scale Weight | 350 g |
| Vital Wheat Gluten | 2% | Glimek Moulder | Typical settings for dough piece |
| Salt | 1.5% | Proof temperature | 40° C./90% humidity |
| Wholemeal flour, Acasia | 100% | Proof time | 60 min |
| Water | 67% | Special treatments | no, medium or high shock |
| | | Deck Oven | 245/235° C. 25 min | pieces in tins were not subjected to any shock-treatment. All dough pieces, with and without shock-treatment were baked. After baking, the specific volume of breads made from the doughs subjected to 'no shock', 'medium shock' and 'high shock', was established using the laser volumeter from TexVol instrument (Perten).

The results in Table 3 show that breads prepared with a variant lipase comprising a substitution (D295S and V179M), (D295N and V179M), (D295S, I113H and V179M), (D295G and I113T), (D295N and I113N), (D295N, I113T, V179M, and N112D), (D295S, I113H, V179M, and I284M), (D295N and I113T), (D295S, I113T, V179M, and I284M), (D295S, I113T, V179M, N121D), (D295S, I113T and V179M), (D295S and I113N), or (D295N and I284T) had an increased bread volume after the doughs were subjected to 'medium shock' or 'high shock' as compared to the volume of breads made with Panamore® Golden (reference polypeptide comprising the mature amino acid sequence of SEQ ID NO:1). Some variants (No. 7, 8, 12, 13, 14 and 15 in Table 3) also had and increased volume as compared to the volume of breads made with Panamore® Golden without shock treatment.

TABLE 3

Relative volume (Max LV) of wholemeal bread using unshocked and shocked doughs made with lipase variants (PAN2 and NBL) as compared to the volume of breads made with Panamore ® Golden (reference protein)

| No° | Variant | Substitutions | Bread from 'unshocked' dough | | Bread from 'medium shocked' dough | | Bread from 'high shocked' dough | |
|---|---|---|---|---|---|---|---|---|
| | | | Max LV* (%) | Enzyme (GalLU/kg) | Max LV* (%) | Enzyme (GalLU/kg) | Max LV* (%) | Enzyme (GalLU/kg) |
| 1 | PAN2_R2_T1_13 | D295S; V179M | 109 | 1098 | 102 | 186 | 101 | 186 |
| 2 | PAN2_R2_T1_14 | D295N; V179M | 96 | 693 | 108 | 1248 | 103 | 1248 |
| 3 | PAN2_R2_T1_33 | D295S; I113H; V179M | 97 | 248 | 104 | 497 | 105 | 497 |
| 4 | PAN2_R2_T1_10 | D295N; I113T; V179M; N121D | 97 | 464 | 108 | 928 | 106 | 928 |
| 5 | PAN2_R2_T1_57 | D295S; I113H; V179M; I284M | 98 | 588 | 108 | 588 | 107 | 588 |
| 6 | PAN2_R2_T1_26 | D295N; I284T | 96 | 2033 | 109 | 1356 | 109 | 1356 |
| 7 | PAN2_R2_T1_53 | D295S; I113T; V179M; I284M | 101 | 272 | 109 | 832 | 109 | 832 |
| 8 | PAN2_R2_T1_61 | D295S; I113T; V179M; N121D | 101 | 245 | 108 | 667 | 110 | 667 |
| 9 | PAN2_R2_T1_29 | D295S; I113T; V179M; | 98 | 214 | 113 | 427 | 113 | 427 |
| 10 | PAN2_R2_T3_85 | D295S; I113N | 100 | 468 | 111 | 936 | 117 | 580 |
| 11 | NBL_R2_T1_25 | D295N; V179M | 98 | 271 | 104 | 271 | 103 | 271 |
| 12 | NBL_R2_T1_15 | D295G; I113T | 103 | 190 | 108 | 190 | 105 | 78 |
| 13 | NBL50_R2_T1-17 | D295N; I113N | 101 | 386 | 107 | 386 | 106 | 585 |
| 14 | NBL50_R2_T1-13 | D295N; I113T | 101 | 257 | 109 | 514 | 108 | 514 |
| 15 | NBL_R2_T1_37 | D295N; I284T | 103 | 438 | 113 | 545 | 118 | 545 |

Max LV* = (maximum specific volume of bread prepared with lipase variant enzyme)/(specific volume of bread prepared with Panamore at 20 ppm) × 100%

Example 3: Effect Variant Lipases (PAN2, and NBL) on the Volume of Bread Made from Flour with Added Free Fatty Acid A white flour stress-test was carried out with recipe and process conditions as shown in Table 4.

TABLE 4

Process conditions white flour stress-test.

| Formulation: | | Process: | |
|---|---|---|---|
| Compressed Yeast | 5% | Diosna SP12 mixer | 400 turns 25 Hz + 36 Wh/kg 50 Hz |
| Ascorbic Acid | 100 ppm | Dough temp after mix | 28-29° C. |
| Amylase, Bakezyme ® P500 | 2 pm | Rest/bench time | 10 min |
| Xylanase, Bakezyme ® HSP6000 | 54 ppm | Scale Weight | 300 g |
| Salt | 1.5% | Glimek Moulder | Typical settings for dough piece |
| White flour, Kolibri | 100% | Proof temperature | 40° C./90% humidity |
| Water | 58% | Proof time | 60 min |
| Linoleic Acid | 0-0.2% | Special treatments | no, medium or high shock |
| | | Deck Oven | 245/235° C. 25 min |

White flour (Kolibri) was from Meneba, compressed yeast (Koningsgist) was from AB Mauri, amylase Bakezyme® P500 and xylanase Bakezyme® HSP6000) were from DSM Food Specialties, linoleic acid was from a general chemical supplier and other materials were from general bakery suppliers. Addition of materials was by bakers' percent, or ppm, that is on a flour weight basis. Lipase was mixed together with the other ingredients. The amount and effect of variant lipase was assessed against an optimal dose of Panamore Golden of 20 ppm for this application, using dose ranges of the variants to determine optimal use levels for these. The amount of variant lipase that resulted in the maximum volume of bread, the optimal dose, was used in the baking trial.

Dough was prepared from batches of 2 kg of flour, to form at least 6×300 g dough pieces after moulding which were placed in appropriate baking-tins (187 mm×96 mm×96 mm). After proofing, at least 4 doughs in their respective tins were subjected to mechanical jarring by a 250 g metal ball, rolling down a track set at around 45° using bespoke apparatus, running into the tins containing the doughs; for a so-called 'medium shock', the track was set at height of around 310 mm, while for a so-called 'high shock', the track was set at a height of around 600 mm. At least 2 dough pieces in tins were not subjected to any shock-treatment All dough pieces, with and without shock-treatment were baked. After baking, the specific volume of breads, made from the doughs subjected to 'no shock', 'medium shock' and 'high shock', was established using the laser volumeter from TexVol instrument (Perten).

The results in Table 5 show that the bread volume of the breads prepared with a NBL variant lipase of SEQ ID NO: 3 (i.e. the mature amino acid sequence of SEQ ID NO: 1 comprising to prolines at position 305 and 306) comprising the substitutions (D295G, I113T) and added linoleic acid after shock treatment of the corresponding dough was higher as compared to the volume of breads prepared in a similar way with the reference lipase in Panamore® Golden at 20 and 40 ppm.

The results in Table 6 show that the volume of breads prepared with the PAN2 variant lipase of SEQ ID NO: 1 comprising the amino acid substitutions (D295S, I113N) and added linoleic acid after shock treatment of the corresponding dough decreased to a lesser extent than the volume of bread prepared with the reference lipase in Panamore® Golden at 20 ppm. The dough made with the variant lipase in Table 6 showed an increased shock resistance as compared to the dough made with the reference lipase.

TABLE 5

Volume of bread (ml/g) made from dough with 0, 0.1% and 0.2% linoleic acid and different (contents of) lipases. The doughs were subjected to no, medium or high shock treatment.

| Shock treatment | Added linoleic acid (%) | Panamore 20 ppm | Panamore 40 ppm | Lipase variant (NBL_R2_T1_15; D295G, I113T plus 305P-306P) (GalLU/kg) | | |
|---|---|---|---|---|---|---|
| | | | | 190 | 285 | 380 |
| None | 0 | 7.5 | | 7.2 | 7.1 | 7.3 |
| Medium | 0 | 7.1 | | 7.0 | 7.1 | 7.1 |
| High | 0 | 6.7 | | 6.6 | 6.5 | 6.6 |
| None | 0.1 | 7.0 | | 7.6 | 7.4 | 7.3 |
| Medium | 0.1 | 6.0 | | 6.7 | 6.7 | 6.6 |
| High | 0.1 | 4.7 | | 5.9 | 6.2 | 5.9 |
| None | 0.2 | 6.5 | 6.6 | 7.1 | 6.0 | |
| Medium | 0.2 | 5.5 | 5.8 | 6.3 | 6.3 | |
| High | 0.2 | 4.7 | 4.6 | 5.2 | 5.6 | |

TABLE 6

Volume of bread (ml/g) made from dough with 0, 0.1% and 0.2% linoleic acid and different (contents of) lipases. The doughs were subjected to no, medium or high shock treatment.

| Shock treatment | Added linoleic acid (%) | Panamore 20 ppm | Lipase variant (Pan2_R2_T3_85; D295S, I113N) (GalLU/kg) | | |
|---|---|---|---|---|---|
| | | | 223 | 468 | 691 |
| None | 0 | 7.7 | 7.2 | 7.1 | 7.2 |
| Medium | 0 | 7.4 | 6.9 | 6.8 | 6.7 |
| High | 0 | 6.8 | 6.0 | 6.0 | 6.0 |
| None | 0.1 | 7.3 | 6.4 | 7.0 | 7.0 |
| Medium | 0.1 | 6.9 | 6.3 | 6.8 | 6.7 |
| High | 0.1 | 6.2 | 5.9 | 6.2 | 6.3 |
| None | 0.2 | 7.3 | 6.0 | 6.5 | 7.0 |
| Medium | 0.2 | 6.3 | 5.4 | 5.9 | 6.4 |
| High | 0.2 | 5.8 | 5.2 | 5.5 | 5.9 |

Example 4: Effect of Variant Lipases of SEQ ID NO: 6 on the Volume of Bread Made from Flour with Added Free Fatty Acid To test whether the amino acid substitutions that were made in SEQ ID NO: 1 have a similar effect on the volume of bread as disclosed in Examples 2 and 3 in a different lipase, similar amino acid substitutions were made in a lipase according to SEQ ID NO: 6. The mature amino acid sequence of SEQ ID NO: 1 has 76.8% identity to the mature amino acid sequence of SEQ ID NO: 6, and the full length amino acid sequences of SEQ ID NO: 1 and SEQ ID NO: 6 have a sequence identity of 78.3%, determined according to the alignment algorithm as defined herein.

Three variant lipases of SEQ ID NO: 6 comprising the amino acid substitutions (I113N, D295S). (I284T. D295N) and (I113T, 295G) were prepared as described in Example 1 and were named LP02, LPV05 and LPV06. The parent lipase (the mature amino acid sequence SEQ ID NO: 6) was named LPV01.

A white flour bakery stress-test was carried out with the recipe and process conditions as shown in Table 3, with the difference that linoleic acid was added at 0.3% w/w instead of 0-0.2 w/w %, using materials and procedures described for Example 3

The variant lipases LP02, LPV05 and LPV06 were benchmarked against LPV01 as well as the commercial Lipopan® F product at 40, 60 and 80 ppm, i.e. 184, 276 and 368 Gall. U/kg respectively. The amount and effect of variant lipase was assessed against an optimal dose of Lipopan® F for this application, using dose ranges of the variants to determine optimal use levels for of the variant lipase. The amount of variant lipase that resulted in the maximum volume of bread, the optimal dose, was used in the baking trial. The baking trials were performed in three separate sets.

The results in Table 7 show that breads made from doughs that were prepared with LPV02, LP05 or LPV06 resulted in a higher volume LPV01 after medium and high shock treatment as compared to all doses of Lipopan® F. This shows that the doughs made with variant lipases comprising an amino acid sequence which has at least 70% identity to SEQ ID NO: 1 or SEQ ID NO: 6 and comprising at least the amino acid substitutions as disclosed herein, such as (I113N, D295S), (I284T, D295N) or (I113T, D295G) resulted in an increased volume of bread as compared to a reference polypeptide

TABLE 7

Volume of bread (ml/g) made from dough with 0.3% linoleic acid and different lipases. The doughs were subjected to no, medium or high shock treatment.

| | | | Baked Volume of bread (ml/g) | | |
|---|---|---|---|---|---|
| Set | Lipase added | Enzyme dose GalLU/kg | No shock treatment | Medium shock treatment | High shock treatment |
| 1 | Lipopan F | 184 | 6.0 | 4.9 | 4.3 |
| | Lipopan F | 276 | 6.1 | 5.3 | 4.5 |
| | Lipopan F | 368 | 6.5 | 5.5 | 4.7 |
| | LPV02 I113N, D295S | 645 | 6.1 | 5.8 | 4.9 |
| 2 | None (blank) | 0 | 5.5 | 4.8 | 4.6 |
| | Lipopan F | 276 | 6.1 | 5.1 | 4.6 |
| | Lipopan F | 368 | 6.3 | 5.4 | 4.5 |
| 3 | Lipopan F | 276 | 6.5 | 5.3 | 4.2 |
| | LPV01; wildtype | 369 | 6.3 | 5.4 | 4.5 |
| | LPV05; I284T, D295N + 305P and 306P | 844 | 6.4 | 5.9 | 5.0 |
| | LPV06; I113T, D295G | 1350 | 6.3 | 5.8 | 5.0 |

The invention claimed is:

1. A variant polypeptide having a lipase activity, wherein the polypeptide is selected from the group consisting of:
   i. a polypeptide which comprises an amino acid sequence which has at least 90% identity to a mature amino acid sequence comprising amino acids 34 to 304 of SEQ ID NO: 1, wherein the polypeptide comprises an amino acid substitution at position 295 and at least one further amino acid substitution at position 113, 121, 179 and/or 284, wherein the positions are defined with reference to SEQ ID NO: 1;
   ii. the polypeptide according to i), wherein the amino acid substitution at position 295 is D295G, D295N or D295S and the at least one further amino acid substitution at position 113 is I113H, I113N or I113T, at position 121 the amino acid substitution is N121D, at position 179 the amino acid substitution is V179M, and/or at position 284 the amino acid substitution is I284M or I284T;
   iii. a polypeptide which has at least 90% identity to a mature amino acid sequence comprising amino acids 34 to 304 of SEQ ID NO: 1, wherein the polypeptide comprises amino acid substitutions (D295S and V179M), (D295N and V179M), (D295S, I113H and V179M), (D295G and I113T), (D295N and I113N), (D295N, I113T, V179M, and N112D), (D295S, I113H, V179M, and I284M), (D295N and I113T), (D295S, I113T, V179M, and I284M), (D295S, I113T, V179M, N121D), (D295S, I113T and V179M), (D295S and I113N), or (D295N and I284T), wherein the substitutions are defined with reference to SEQ ID NO: 1;
   iv. the polypeptide according to i)-iii), wherein the polypeptide comprises an insertion of one or more amino acid(s) after position 304, wherein the position is defined with reference to SEQ ID NO: 1; and
   v. the polypeptide according to iv), wherein the mature amino acid sequence of SEQ ID NO: 1 comprises the insertion.

2. The polypeptide according to claim 1, wherein the insertion comprises a proline at position 305 and 306.

3. The variant polypeptide according to claim 1, wherein the polypeptide, when used in dough, improves shock resistance of dough, dough stability and/or increases the volume of a baked product made from the dough as compared to the shock resistance, dough stability and/or volume of a baked product made from a dough comprising a reference polypeptide, wherein said reference polypeptide is the mature amino acid sequence of SEQ ID NO: 1.

4. A nucleic acid encoding a polypeptide having lipase activity according to claim 1, wherein optionally the nucleic acid has at least 70% 90% identity to SEQ ID NO: 2 or SEQ ID NO: 4, wherein the nucleic acid comprises a mutation encoding an amino acid substitution D295G, D295N or D295S and at least one further amino acid substitution I113H, I113N or I113T, and/or N121D, and/or V179M, and/or I284M or I284T, wherein the substitutions are defined with reference to SEQ ID NO: 1.

5. An expression vector comprising a nucleic acid according to claim 4 operably linked to at least one control sequence that direct expression of the polypeptide in a host cell.

6. A recombinant host cell comprising a nucleic acid according to claim 4, or an expression vector comprising said nucleic acid.

7. A method for preparation of a polypeptide according to claim 1, comprising cultivating a host cell in a suitable fermentation medium, under conditions that allow expression of the polypeptide, and optionally recovering the polypeptide.

8. A composition comprising a polypeptide according to claim 1.

9. A process for preparing a dough comprising adding a polypeptide according to claim 1 to the dough.

10. A dough comprising a variant polypeptide according to claim 1.

11. A process for preparing a baked product comprising baking a dough according to claim 10.

12. A product comprising a variant polypeptide according to claim 1 to increase shock resistance, improve stability of a dough and/or increase the volume of bread.

13. A process for increasing volume of a baked product, comprising
preparing a dough comprising a polypeptide according to claim 1,
subjecting the dough to a shock treatment, and
baking the dough,
wherein the volume of the baked product is increased as compared to the volume of a baked product prepared from a dough comprising a reference polypeptide, wherein said reference polypeptide is the mature amino acid sequence of SEQ ID NO: 1.

14. The process according to claim 13, wherein the dough and/or the baked product comprises wholemeal flour and/or a flour comprising a free fatty acid content of between 0.01 to 0.8 w/w %.

15. The variant polypeptide according to claim 1, wherein the polypeptide of i) and iii) comprises an amino acid sequence which has at least 95% identity to a mature amino acid sequence comprising amino acids 34 to 304 of SEQ ID NO: 1.

16. The variant polypeptide according to claim 1, wherein the polypeptide of i) and iii) comprises an amino acid sequence which has at least 97% identity to a mature amino acid sequence comprising amino acids 34 to 304 of SEQ ID NO: 1.

17. The variant polypeptide according to claim 1, wherein the polypeptide of i) and iii) comprises an amino acid sequence which has at least 99% identity to a mature amino acid sequence comprising amino acids 34 to 304 of SEQ ID NO: 1.

18. The variant polypeptide according to claim 1, wherein the polypeptide of i) and iii) comprises an amino acid sequence which has 100% identity to a mature amino acid sequence comprising amino acids 34 to 304 of SEQ ID NO: 1.

* * * * *

SEQUENCE LISTING

<160> NUMBER OF SEQ ID NOS: 7

<210> SEQ ID NO 1
<211> LENGTH: 346
<212> TYPE: PRT
<213> ORGANISM: Artificial Sequence
<220> FEATURE:
<223> OTHER INFORMATION: Amino acid sequence of a polypeptide having lipase activity

<400> SEQUENCE: 1

Met Leu Leu Leu Ser Leu Leu Ser Ile Val Thr Leu Ala Val Ala Ser
1               5                   10                  15

Pro Leu Ser Val Glu Glu Tyr Ala Lys Ala Leu Glu Glu Arg Ala Val
            20                  25                  30

Thr Val Ser Ser Ser Glu Leu Asn Asn Phe Lys Phe Tyr Ile Gln His
        35                  40                  45

Gly Ala Ala Ala Tyr Cys Asn Ser Glu Thr Ala Ala Gly Ala Asn Val
    50                  55                  60

Thr Cys Thr Gly Asn Ala Cys Pro Glu Ile Glu Ala Asn Gly Val Thr
65                  70                  75                  80

Val Val Ala Ser Phe Thr Gly Thr Lys Thr Gly Ile Gly Gly Tyr Val
                85                  90                  95

Ser Thr Asp Asn Thr Asn Lys Glu Ile Val Leu Ser Phe Arg Gly Ser
            100                 105                 110

Ile Asn Ile Arg Asn Trp Leu Thr Asn Leu Asp Phe Gly Gln Asp Asp
        115                 120                 125

Cys Ser Leu Thr Ser Gly Cys Gly Val His Ser Gly Phe Gln Arg Ala
    130                 135                 140

Trp Glu Glu Ile Ala Asp Asn Leu Thr Ala Ala Val Ala Lys Ala Lys

```
            145                 150                 155                 160
Thr Ala Asn Pro Asp Tyr Lys Val Val Ala Thr Gly His Ser Leu Gly
                165                 170                 175

Gly Ala Val Ala Thr Leu Ala Gly Ala Asn Leu Arg Ala Ala Gly Thr
            180                 185                 190

Pro Leu Asp Ile Tyr Thr Tyr Gly Ser Pro Arg Val Gly Asn Ala Glu
            195                 200                 205

Leu Ala Glu Phe Ile Ser Asn Gln Thr Gly Gly Glu Phe Arg Val Thr
            210                 215                 220

His Gly Asp Asp Pro Val Pro Arg Leu Pro Pro Leu Ile Phe Gly Tyr
225                 230                 235                 240

Arg His Thr Ser Pro Glu Tyr Trp Leu Asp Gly Ser Gly Gly Asp Lys
                245                 250                 255

Ile Asn Tyr Thr Ile Asn Asp Ile Lys Val Cys Glu Gly Ala Ala Asn
            260                 265                 270

Leu Gln Cys Asn Gly Gly Thr Leu Gly Leu Asp Ile Ala Ala His Leu
            275                 280                 285

His Tyr Phe Gln Ala Thr Asp Ala Cys Asn Ala Gly Gly Phe Ser Trp
            290                 295                 300

Arg Arg Tyr Arg Ser Ala Glu Ser Val Asp Lys Arg Ala Thr Met Thr
305                 310                 315                 320

Asp Ala Glu Leu Glu Lys Lys Leu Asn Ser Tyr Val Gln Met Asp Lys
                325                 330                 335

Glu Tyr Val Lys Asn Asn Gln Ala Arg Ser
                340                 345

<210> SEQ ID NO 2
<211> LENGTH: 1041
<212> TYPE: DNA
<213> ORGANISM: Artificial Sequence
<220> FEATURE:
<223> OTHER INFORMATION: Nucleotide sequence encoding a lipase of SEQ ID
      NO: 1

<400> SEQUENCE: 2
atgcttctcc tctccctcct ctccattgtc accctcgctg ttgcttctcc tctgtccgtt     60
gaggagtacg ccaaggccct cgaggagcgt gccgtcaccg tctcctcctc cgagctcaac    120
aacttcaagt tctacatcca gcacggtgct gctgcctact gcaactccga gactgctgct    180
ggtgccaacg tcacctgcac tggcaacgcc tgccccgaga ttgaggccaa cggtgtcacc    240
gttgttgcct ccttcactgg taccaagact ggtatcggtg ctacgtctc acccgacaac    300 accaacaagg agatcgtcct ttctttccgt ggcagcatca acatccgcaa ctggctgacc    360
aacctggact tcggccagga tgactgctct ctgacctccg gctgcggtgt ccactccggt    420
ttccagcgtg cctgggagga gattgccgac aacctgaccg ctgctgttgc caaggccaag    480
actgccaacc ccgactacaa ggttgttgcc actggccact ccctgggtgg tgctgttgcc    540
accctggctg gtgccaacct ccgtgctgct ggtaccccc tcgacatcta cacctacggc    600
tctccccgtg tcggcaacgc cgagcttgct gagttcatct ccaaccagac tggtggtgag    660
ttccgtgtca cccacggtga tgaccccgtc cccgtcttc tcctctgat cttcggctac    720 cgccacacct cccccgagta ctggctcgat ggcagcggtg gtgacaagat caactacacc    780
atcaacgaca tcaaggtctg cgagggtgct gccaacctgc agtgcaacgg tggtaccctg    840
ggactcgaca ttgctgctca cctgcactac ttccaggcca ctgatgcctg caacgccggt    900
```

```
ggtttcagct ggcgccgcta ccgctctgct gagagcgttg acaagcgtgc caccatgact      960
gatgctgagc tcgagaagaa gctcaacagc tacgtgcaga tggacaagga gtacgtcaag     1020
aacaaccagg ctcgctccta a                                                1041
```

<210> SEQ ID NO 3
<211> LENGTH: 348
<212> TYPE: PRT
<213> ORGANISM: Artificial Sequence
<220> FEATURE:
<223> OTHER INFORMATION: Amino acid sequence of a lipase of SEQ ID NO: 1
      containing two proline residues at position 304

<400> SEQUENCE: 3

```
Met Leu Leu Leu Ser Leu Leu Ser Ile Val Thr Leu Ala Val Ala Ser
1               5                   10                  15

Pro Leu Ser Val Glu Glu Tyr Ala Lys Ala Leu Glu Glu Arg Ala Val
                20                  25                  30

Thr Val Ser Ser Ser Glu Leu Asn Asn Phe Lys Phe Tyr Ile Gln His
            35                  40                  45

Gly Ala Ala Ala Tyr Cys Asn Ser Glu Thr Ala Ala Gly Ala Asn Val
        50                  55                  60

Thr Cys Thr Gly Asn Ala Cys Pro Glu Ile Glu Ala Asn Gly Val Thr
65                  70                  75                  80

Val Val Ala Ser Phe Thr Gly Thr Lys Thr Gly Ile Gly Gly Tyr Val
                85                  90                  95

Ser Thr Asp Asn Thr Asn Lys Glu Ile Val Leu Ser Phe Arg Gly Ser
                100                 105                 110

Ile Asn Ile Arg Asn Trp Leu Thr Asn Leu Asp Phe Gly Gln Asp Asp
            115                 120                 125

Cys Ser Leu Thr Ser Gly Cys Gly Val His Ser Gly Phe Gln Arg Ala
        130                 135                 140

Trp Glu Glu Ile Ala Asp Asn Leu Thr Ala Ala Val Ala Lys Ala Lys
145                 150                 155                 160

Thr Ala Asn Pro Asp Tyr Lys Val Val Ala Thr Gly His Ser Leu Gly
                165                 170                 175

Gly Ala Val Ala Thr Leu Ala Gly Ala Asn Leu Arg Ala Ala Gly Thr
                180                 185                 190

Pro Leu Asp Ile Tyr Thr Tyr Gly Ser Pro Arg Val Gly Asn Ala Glu
            195                 200                 205

Leu Ala Glu Phe Ile Ser Asn Gln Thr Gly Gly Glu Phe Arg Val Thr
        210                 215                 220

His Gly Asp Asp Pro Val Pro Arg Leu Pro Pro Leu Ile Phe Gly Tyr
225                 230                 235                 240

Arg His Thr Ser Pro Glu Tyr Trp Leu Asp Gly Ser Gly Gly Asp Lys
                245                 250                 255

Ile Asn Tyr Thr Ile Asn Asp Ile Lys Val Cys Glu Gly Ala Ala Asn
                260                 265                 270

Leu Gln Cys Asn Gly Gly Thr Leu Gly Leu Asp Ile Ala Ala His Leu
            275                 280                 285

His Tyr Phe Gln Ala Thr Asp Ala Cys Asn Ala Gly Gly Phe Ser Trp
        290                 295                 300

Pro Pro Arg Arg Tyr Arg Ser Ala Glu Ser Val Asp Lys Arg Ala Thr
305                 310                 315                 320

Met Thr Asp Ala Glu Leu Glu Lys Lys Leu Asn Ser Tyr Val Gln Met
                325                 330                 335
```

Asp Lys Glu Tyr Val Lys Asn Asn Gln Ala Arg Ser
            340                 345

<210> SEQ ID NO 4
<211> LENGTH: 1047
<212> TYPE: DNA
<213> ORGANISM: Artificial Sequence
<220> FEATURE:
<223> OTHER INFORMATION: Nucleotide sequence encoding a lipase according
      to SEQ ID NO: 3

<400> SEQUENCE: 4

```
atgcttctcc tctccctcct ctccattgtc accctcgctg ttgcttctcc tctgtccgtt      60
gaggagtacg ccaaggccct cgaggagcgt gccgtcaccg tctcctcctc cgagctcaac     120
aacttcaagt tctacatcca gcacggtgct gctgcctact gcaactccga gactgctgct     180
ggtgccaacg tcacctgcac tggcaacgcc tgccccgaga ttgaggccaa cggtgtcacc     240
gttgttgcct ccttcactgg taccaagact ggtatcggtg ctacgtctc caccgacaac      300
accaacaagg agatcgtcct ttctttccgt ggcagcatca acatccgcaa ctggctgacc     360
aacctggact tcggccagga tgactgctct ctgacctccg gctgcggtgt ccactccggt     420
ttccagcgtg cctgggagga gattgccgac aacctgaccg ctgctgttgc caaggccaag    480
actgccaacc ccgactacaa ggttgttgcc actggccact ccctgggtgg tgctgttgcc    540
accctggctg gtgccaacct ccgtgctgct ggtaccccc tcgacatcta cacctacggc      600
tctccccgtg tcggcaacgc cgagcttgct gagttcatct ccaaccagac tggtggtgag    660
ttccgtgtca cccacggtga tgaccccgtc cccgtcttc ctcctctgat cttcggctac      720
cgccacacct cccccgagta ctggctcgat ggcagcggtg tgacaagat caactacacc      780
atcaacgaca tcaaggtctg cgagggtgct gccaacctgc agtgcaacgg tggtaccctg    840
ggactcgaca ttgctgctca cctgcactac ttccaggcca ctgatgcctg caacgccggt    900
ggtttcagct ggcctccccg ccgctaccgc tctgctgaga gcgttgacaa gcgtgccacc    960
atgactgatg ctgagctcga gaagaagctc aacagctacg tgcagatgga caaggagtac   1020
gtcaagaaca accaggctcg ctcctaa                                        1047
```

<210> SEQ ID NO 5
<211> LENGTH: 13
<212> TYPE: DNA
<213> ORGANISM: Artificial Sequence
<220> FEATURE:
<223> OTHER INFORMATION: Modified translational initiation sequence of
      glucoamylase glA promotor

<400> SEQUENCE: 5
caccgtcaaa atg                                                         13

<210> SEQ ID NO 6
<211> LENGTH: 346
<212> TYPE: PRT
<213> ORGANISM: Artificial Sequence
<220> FEATURE:
<223> OTHER INFORMATION: Fusarium oxysporum

<400> SEQUENCE: 6

Met Leu Leu Leu Pro Leu Leu Ser Ala Ile Thr Leu Ala Val Ala Ser
1               5                   10                  15

Pro Val Ala Leu Asp Asp Tyr Val Asn Ser Leu Glu Glu Arg Ala Val
            20                  25                  30

```
Gly Val Thr Thr Thr Asp Phe Ser Asn Phe Lys Phe Tyr Ile Gln His
            35                  40                  45

Gly Ala Ala Ala Tyr Cys Asn Ser Glu Ala Ala Gly Ser Lys Ile
 50                  55                  60

Thr Cys Ser Asn Asn Gly Cys Pro Thr Val Gln Gly Asn Gly Ala Thr
 65                  70                  75                  80

Ile Val Thr Ser Phe Val Gly Ser Lys Thr Gly Ile Gly Gly Tyr Val
                 85                  90                  95

Ala Thr Asp Ser Ala Arg Lys Glu Ile Val Val Ser Phe Arg Gly Ser
                100                 105                 110

Ile Asn Ile Arg Asn Trp Leu Thr Asn Leu Asp Phe Gly Gln Glu Asp
            115                 120                 125

Cys Ser Leu Val Ser Gly Cys Gly Val His Ser Gly Phe Gln Arg Ala
            130                 135                 140

Trp Asn Glu Ile Ser Ser Gln Ala Thr Ala Ala Val Ala Ser Ala Arg
145                 150                 155                 160

Lys Ala Asn Pro Ser Phe Asn Val Ile Ser Thr Gly His Ser Leu Gly
                165                 170                 175

Gly Ala Val Ala Val Leu Ala Ala Ala Asn Leu Arg Val Gly Gly Thr
            180                 185                 190

Pro Val Asp Ile Tyr Thr Tyr Gly Ser Pro Arg Val Gly Asn Ala Gln
            195                 200                 205

Leu Ser Ala Phe Val Ser Asn Gln Ala Gly Gly Glu Tyr Arg Val Thr
            210                 215                 220

His Ala Asp Asp Pro Val Pro Arg Leu Pro Leu Ile Phe Gly Tyr
225                 230                 235                 240

Arg His Thr Thr Pro Glu Phe Trp Leu Ser Gly Gly Gly Asp Lys
                245                 250                 255

Val Asp Tyr Thr Ile Ser Asp Val Lys Val Cys Glu Gly Ala Ala Asn
            260                 265                 270

Leu Gly Cys Asn Gly Gly Thr Leu Gly Leu Asp Ile Ala Ala His Leu
            275                 280                 285

His Tyr Phe Gln Ala Thr Asp Ala Cys Asn Ala Gly Gly Phe Ser Trp
290                 295                 300

Arg Arg Tyr Arg Ser Ala Glu Ser Val Asp Lys Arg Ala Thr Met Thr
305                 310                 315                 320

Asp Ala Glu Leu Glu Lys Lys Leu Asn Ser Tyr Val Gln Met Asp Lys
                325                 330                 335

Glu Tyr Val Lys Asn Asn Gln Ala Arg Ser
            340                 345
```

<210> SEQ ID NO 7
<211> LENGTH: 1041
<212> TYPE: DNA
<213> ORGANISM: Artificial Sequence
<220> FEATURE:
<223> OTHER INFORMATION: Nucleotide sequence encoding Fusarium oxysporum
      lipase that was codon-pair optimized for expression in Aspergillus
      niger

<400> SEQUENCE: 7
atgctcctcc ttcctctcct ctccgccatc accctggccg ttgcctcccc cgttgctctc      60
gatgactacg tcaactccct cgaggagcgt gccgtcggtg tcaccaccac cgacttctcc     120
aacttcaagt tctacatcca gcacggtgct gctgcctact gcaactccga ggctgctgct     180

```
ggcagcaaga tcacctgctc caacaacggc tgccccaccg tccagggcaa cggtgccacc      240
attgtcacct ccttcgtcgg cagcaagact ggtatcggtg gctacgttgc caccgactct      300
gctcgcaagg agattgtcgt ctccttccgt ggcagcatca acatccgcaa ctggctgacc      360
aacctggact tcggccagga agactgctct cttgtctccg gctgcggtgt ccactccggt      420
ttccagcgtg cctggaacga gatctcctcc caggccactg ctgccgttgc ttctgctcgc      480
aaggccaacc cctccttcaa cgtcatctcc actggccact ctcttggtgg tgctgttgct      540
gtccttgctg ctgccaacct ccgtgtcggt ggtactcccg ttgacatcta cacctacggc      600
agccctcgtg tcggcaacgc ccagctgtct gctttcgtct ccaaccaggc tggtggtgaa      660
taccgtgtca cccacgccga tgacccgtt ccccgtcttc ctcctctgat cttcggttac      720
cgccacacca ctcccgagtt ctggctatcc ggtggtggtg gtgacaaggt cgactacacc      780
atctccgatg tcaaggtctg cgagggtgct gccaacctgg gctgcaacgg tggtaccctg      840
ggactcgaca ttgctgctca cctgcactac ttccaggcca ctgatgcctg caacgccggt      900
ggtttcagct ggcgccgcta ccgctctgct gagagcgttg acaagcgtgc caccatgact      960
gatgctgagc tcgagaagaa gctcaacagc tacgtgcaga tggacaagga gtacgtcaag     1020
aacaaccagg ctcgctccta a                                              1041
```